Sept. 5, 1961 A. E. ULRICH Plant Pat. 2,085

STRAWBERRY PLANT

Filed April 14, 1960

INVENTOR
ARNOLD E. ULRICH
BY John W. Adams
ATTORNEY

United States Patent Office

Plant Pat. 2,085
Patented Sept. 5, 1961

2,085
STRAWBERRY PLANT

Arnold E. Ulrich, 600 20th St. SW., Rochester, Minn.

Filed Apr. 14, 1960, Ser. No. 22,379
1 Claim. (Cl. 47—62)

The present invention relates generally to a new and distinct variety of strawberry plant, and more specifically to such a plant which is the result of a planned cross between the Burgundy variety (unpatented), a June bearing plant and the Premier variety (unpatented), also a June bearing plant.

This new variety of strawberry plant was developed and produced on my farm at Rochester, Minnesota, and a large number of plants have been asexually reproduced therefrom by transplanting rooted runner plants therefrom on my said farm.

The object of the cross is to produce a strawberry with the outstanding appearance and quality of the Burgundy variety, and a variety of strawberry plant which would have the ease of growing characteristics of the Premier variety.

The new variety of the present invention embodies the hardy growth characteristics of the Premier in addition to having a berry of excellent quality, the quality of the berry being considered substantially better than that of either plant. The variety is unusually productive and has consistently produced 50 percent more berries per plant than either of its parents.

In the accompanying drawings there is illustrated a berry and a leaf, of typical size and shape. In the said drawings.

Figure 1:
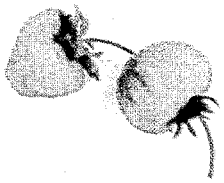
FIG. 1 shows a front elevational view and a side elevational view of a typical berry.
Figure 2:
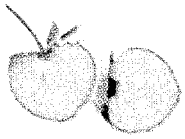
FIG. 2 is a central vertical longitudinal section taken through the berry as shown in FIG. 1.
Figure 3:
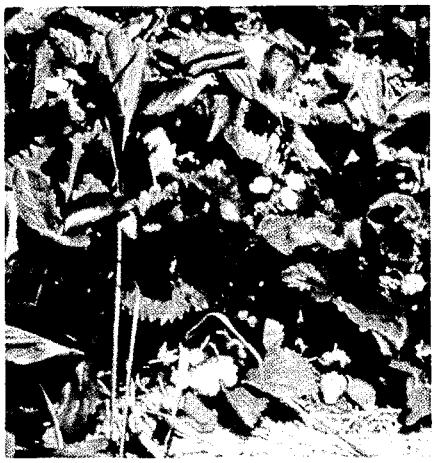
FIG. 3 is a view of a typical plant of the new variety.
Figure 4:
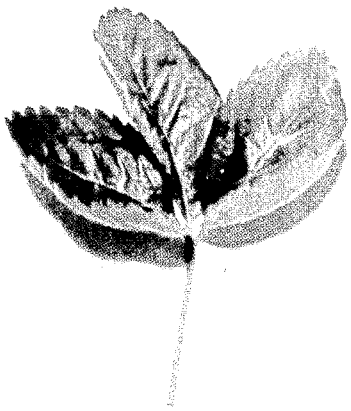
FIG. 4 is an elevational view showing the stem with typical leaves thereon.

Reference is now made to the new variety of strawberry plant, the plant and berry having the following distinctive characteristics which combine to distinguish them from other known varieties.

The plant has been found to be extremely prolific and generally produces 15 or more rooted runner plants from each mother plant by the fall of the year. The plants are extremely hardy, being similar to that of the Premier variety. The root system is generally larger than the Premier variety and unusually great number of fine roots extending therefrom. The plants consistently produce about 50 percent more berries than either of the parent plants.

The berry is generally about the size of the berry obtained from the Premier variety under normal conditions. The color is a bright red, glossy in appearance, and considerably more attractive than the berry of either the Premier or the Burgundy varieties. The surface contour is regular, the shape being almost uniformly conical throughout the entire bearing season. The seeds are small and flush with the surface of the berry. The flesh of the berry is red substantially all the way through and has but a small inner core.

The plants commence bearing about 3 days later than the Premier, the bearing season of the new variety at Rochester, Minnesota being from about June 10 to July 3. As many as five individual fruiting stems normally come directly out of the crown so that each plant will produce about 25 to 30 berries, each stem having generally not more than about 5 or 6 berries. Accordingly, berries produced continue to be of relatively good size throughout the season.

In order to better comprehend the characteristics of the new variety of strawberry plant described herein, a summary of the characteristics is provided, as follows:

*Plant characteristics*

*Root system.*—The root system is relatively large, being larger than the Premier variety and having many fine roots. The plants grow well in medium heavy soil.

*Crown size.*—Similar to the Premier variety.

*Foliage.*—The leaves are similar in shape and color to the Premier variety. There are rarely 4 leaflets on a single petiole, and the leaves are generally cupped upwardly in a fashion similar to that of the Premier variety. The upper surface of the leaf has pubescens, and is generally green with a bluish cast which is similar to the Premier variety. The under surface of the leaflet has a somewhat lighter green color.

*Runners.*—The runner plants are produced in about the same degree of profusion as the Premier variety. Generally, by the fall of the year, mother plants will have produced 15 or more rooted runner plants.

*Flower and stems.*—The flower and fruit stems are generally heavier and more upright than the Premier variety. The flower is generally large and bisexual. Normally, not more than 5 or 6 berries are produced on each stem so that the berries produced throughout the length of the season continue to be of good size. About 5 individual fruiting stems generally come directly out of the crown so that each plant will produce about 25 to 30 berries. It has been found that this will equal about ½ quart.

*Fruit characteristics*

*Size.*—The new variety yields greater amounts of fruit than either of its parents, the fruit bodies being axially curved and having a rounded conical shape. The berry has a sweet but slightly tart flavor. The size of the berry is generally larger than that of either the Premier or the Burgundy varieties, and is almost entirely free of hollow zones such as those which often occur in the early berry of the Premier variety.

*Core.*—The core is normally solid, being generally similar to the flesh of the remainder of the berry. The core is accordingly substantially free from fibers.

The strawberry described above and the plant producing the same may vary in slight details, particularly depending upon the climate, general weather conditions and the type of soil in which they are grown.

What is claimed is:

A new and distinct variety of strawberry plant, substantially as herein shown and described characterized by the outstanding appearance of the fruit which has a medium red bright glossy color with substantially nonconspicuous seeds and having an axially curved rounded conical shape, the plant yielding substantially greater quantities of fruit than either of its parents.

No references cited.